(12) United States Patent
Jimenez Mendoza et al.

(10) Patent No.: US 8,632,732 B2
(45) Date of Patent: Jan. 21, 2014

(54) DEVICE AND METHOD FOR MEASURING THE WATER ACTIVITY OF FOODS

(76) Inventors: Dimas Jimenez Mendoza, Mexico (MX); Ramón Arana Errasqui, Mexico City (MX)

(*) Notice: Subject to any disclaimer, the term of this patent is extended or adjusted under 35 U.S.C. 154(b) by 485 days.

(21) Appl. No.: 12/919,481

(22) PCT Filed: Feb. 28, 2008

(86) PCT No.: PCT/MX2008/000035
§ 371 (c)(1), (2), (4) Date: Aug. 25, 2010

(87) PCT Pub. No.: WO2009/108036
PCT Pub. Date: Sep. 3, 2009

(65) Prior Publication Data
US 2010/0330679 A1    Dec. 30, 2010

(30) Foreign Application Priority Data
Feb. 26, 2008 (MX) .................. MX/A/2008/002699

(51) Int. Cl.
*G01N 21/75* (2006.01)
*G01N 33/02* (2006.01)

(52) U.S. Cl.
USPC ............................. 422/405; 73/73; 436/178

(58) Field of Classification Search
USPC .................. 436/20; 422/405; 73/73
See application file for complete search history.

(56) References Cited

U.S. PATENT DOCUMENTS

| 4,015,463 A * | 4/1977 | Pott ................................. 73/73 |
| 4,215,568 A | 8/1980 | Garber et al. |
| 5,816,704 A | 10/1998 | Campbell et al. |
| 2006/0043300 A1 | 3/2006 | Campbell et al. |

FOREIGN PATENT DOCUMENTS

CA    1209020 A    8/1986

OTHER PUBLICATIONS

PCT/MX08/00035 ISR dated Jul. 2, 2008.

* cited by examiner

*Primary Examiner* — Krishnan S Menon
*Assistant Examiner* — Rebecca M Fritchman
(74) *Attorney, Agent, or Firm* — Matthew J. Lattig; Charter IP, LLC

(57) ABSTRACT

Example embodiments relate a device for measuring the water activity of foods and method for obtaining a water activity measurement. The device includes a container housing the food sample, a disc of permeable material to support a reactive substance which in turn is used to record the water activity level of the food sample (23) being studied. The substance is positioned in the center of the disc. A threaded cover is disposed at a free end of the container. When insulation is provided between the interior and exterior of the container, any water contained in the food sample evaporates and as it passes through the disc. As the water comes into contact with the reactive substance, a color scale records the water activity of the study sample.

9 Claims, 3 Drawing Sheets

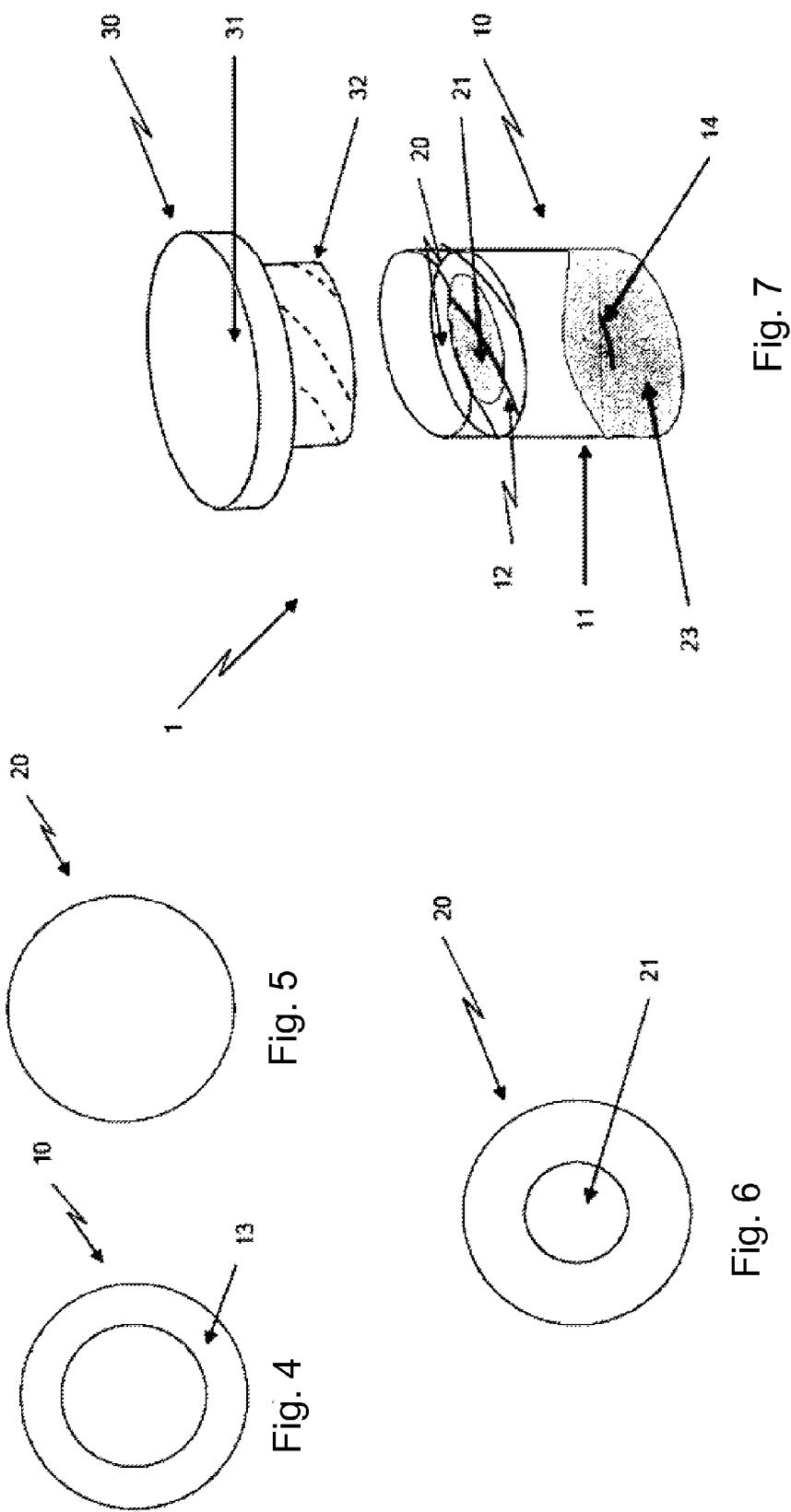

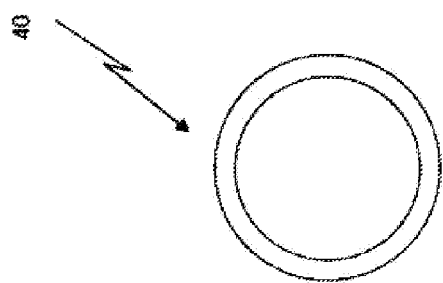
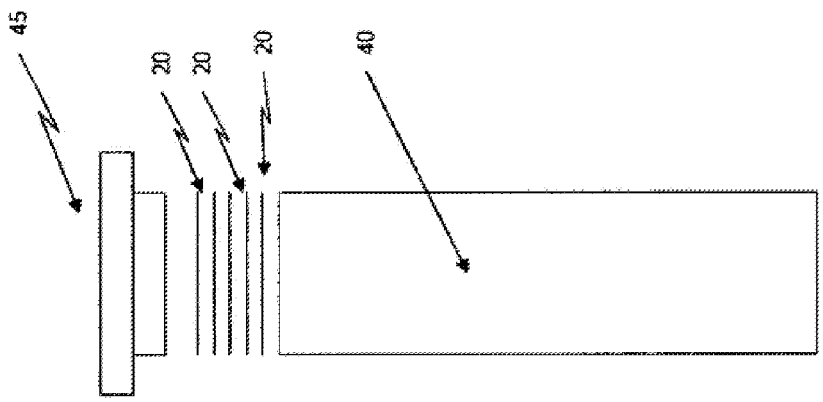
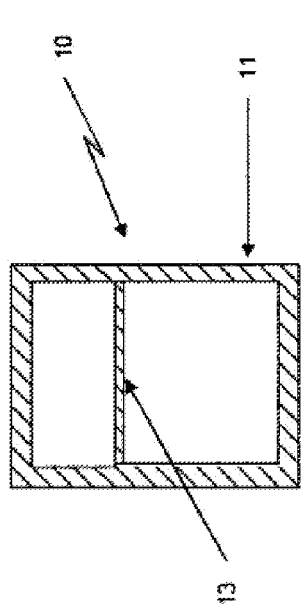
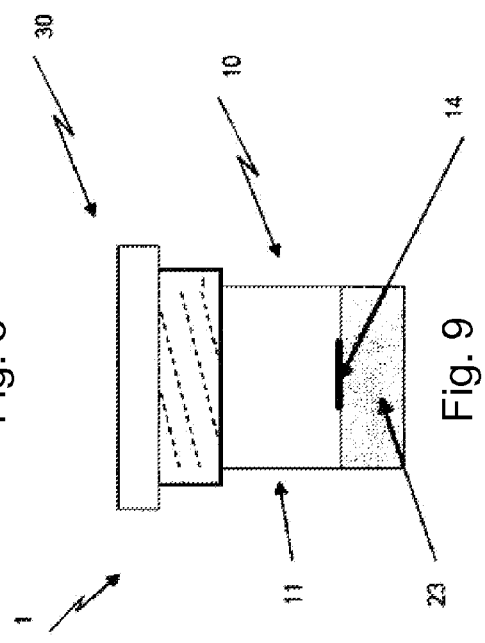
Fig. 11
Fig. 10
Fig. 8
Fig. 9

DEVICE AND METHOD FOR MEASURING THE WATER ACTIVITY OF FOODS

PRIORITY STATEMENT

The present application claims priority to PCT International Application No. PCT/MX08/00035, filed Feb. 28, 2008 by the inventors, and Mexican Patent Application No. MX/a/2008/002699 to the inventors and filed Feb. 26, 2008. The entire contents of each of these applications are hereby incorporated by reference herein.

BACKGROUND

1. Field

The example embodiments in general are related to the field of Food Chemistry; that is, to the study of processes and interactions existing among biological components when foods are manipulated, as considered from a chemical point of view. More particularly, the example embodiments relate to devices and methods for testing water activity of foods, by means of which the stability and useful life of a food can be predicted.

2. Related Art

Water is an essential component of many foods. It can be found at intracellular media or as an extra-cellular component of vegetables and of products of animal origin. Its function must be understood as the one that favors dispersion of different substances, as well as that of a solvent of a great variety of chemical products. The study of water in foods is necessary, because the understanding of its properties and concentration allows, for example, the control of decay chemistry and microbiological activity in foods.

Also, the elimination (drying) or freezing of water are essential for some food conservation methods.

The presence of water in some foods is sometimes understood as a determinant part of their texture, particularly the one named water activity; therefore its analytical measurement in foods is considered as of great importance.

Water activity is defined as the ratio existing between water vapor pressure of a certain food, and the pure water vapor pressure at the same temperature. Generally it is represented by Aw (from "activity of water"). Water activity is a parameter closely related to the moisture of the food, which allows the determination of its conservation and microbial propagation properties.

A more formal definition of water activity, represented by Aw, is:

$Aw = p/po$, where: p is vapor pressure of water in the substance, and po is vapor pressure of pure water, at the same temperature.

In view of the importance that water activity has attained as a criterion for evaluation and control of food safety and quality, a wide diversity of instruments and methods to measure this activity are used; however these devices and instruments are generally complex in their assembly and operation because they use highly sophisticated technology, comprising high-precision sensors, sample retention chambers that are highly sensitive to environmental pressure and temperature conditions, or chemical compounds that need complex manipulation. This result in a limited application of these devices and methods, because they require accurate operating conditions, as well as the attention of specialized personnel; their sophistication level renders them among high-cost devices, hardly accessible to food producers when measurement of water activity of foods produced by them is to be done rapidly, effectively and with a minimum testing cost.

In this sense, Campbell[1] describes an apparatus and a method for measuring activity and condensation temperature of water and temperature; it comprises one compartment where an air sample is measured, one air circulation device, installed inside the compartment, one sensor of sample temperature, one sensor of relative humidity, and one deflector that allows the direct influence of air circulating inside the compartment on the sensor of relative humidity. Another embodiment of this invention comprises the assembly of an air circulation device within the compartment, to force the air inside the compartment so as to reduce the resistance of the limit layer. Still another embodiment of this invention consists in using a temperature control device for controlling inner surface temperatures inside the compartment. Still another embodiment of this invention comprises one sensor for relative humidity of the product, where one sensor of condensation temperature, that can be a resistive or capacitive sensor, is used jointly with a heater and/or a fan for the purpose of shortening the time required to reach equilibrium, and improving accuracy of condensation temperature measurements.

Friedrich[2] describes a device for measuring water activity of foods not containing water, which is used for measuring activity of water in the substances, especially the food substances such as meat and meat products not containing water. This device comprises one lower section and one upper section, detachably connected to the lower section. The lower section contains one or more measuring instruments, including a container for containing the food sample to be analyzed. On the container an instrument support is mounted, to hold the adequate instrument with its respective indicator and a visible scale, and the container has an opening in the upper section. Upper and lower section consists, preferably, of a synthetic foam material, such as hard polystyrol foam.

Finally, and this does not mean that no more documents on status of the art exist reflecting sophisticated inventions developed by men for measuring water activity, but only to clarify which are the antecedents of the invention matter of this patent application, Sharpe[3] describes one instrument for measuring relative humidity or the level of water activity of a food sample, within set limits, that obtains a reading in matter of seconds; the instrument comprises a rough or porous exposition surface, on which there is a pattern of substances named indicators, and each of them are dissolved at a known relative humidity. These indicator substances are applied in such quantities that they are invisible, or nearly invisible, when dry, but they become nearly of entirely visible again when contacting a humid atmosphere, depending on the relative humidity of the atmosphere, referred to as the range of relative humidity covered by indicators that are dissolved. If indicators are applied in the form of decimal fractions corresponding to their relative humidity, the instrument gives a digital reading of relative humidity, directly and with no electronics. In an embodiment, the exposition surface is made of crystal treated with dichlorodimethylsilane once indicators are applied. In other embodiments, exposition surface is a fine porous film made of polymer. In other embodiments, the exhibition is included in a low dish that can be applied to the surface of a food. In a final embodiment, dissolving indicators are mixed with a dye, which is diffused into a porous detachable layer, thus providing a permanent record of moisture or water activity.

Considering the above background, the development of sample and effective methods and devices for determining water activity of foods is essential.

SUMMARY

The example embodiments as described hereafter provide a device for measuring water activity of foods in a rapid and sample manner, using one method that can be applied by anyone interested in knowing the result for water activity of foods, even without having advanced knowledge in the field of food chemistry.

This example device for measuring water activity of foods additionally is configured with a simple construction and no elements requiring special care, such as temperature- or relative humidity sensors.

The example device for measuring water activity of foods that presents accurate results of easy interpretation, and within a time less than one hour.

Moreover, the example embodiments provide for a device for measuring water activity of foods that can be quickly carried to any place where the sample to be studied is found.

BRIEF DESCRIPTION OF THE DRAWINGS

The example embodiments will become more fully understood from the detailed description given herein below and the accompanying drawings, which are given by way of illustration only and thus are not limitative of the example embodiments thereof.

FIG. 4 shows a top plan view of container holding the device (shown in FIG. 1) for measuring the water activity of foods from FIG. 1.

FIG. 5 shows a top plan view of a disc of permeable material that is used as carrier medium for a reactive substance, through which the level of water activity of foods is recorded.

FIG. 6 shows a top plan view of the disc of material shown in FIG. 5, once the reactive substance has been added to it.

FIG. 7 shows a perspective view of the device (shown in FIG. 1) for measuring the water activity of foods, when it is open ad when the sample of food and the disc of permeable material added with the substance have been placed inside the containing vessel.

FIG. 8 shows a crosscut view of device (shown in FIG. 1) container, for measuring water activity of foods.

FIG. 9 shows a front elevation view of the device (shown in FIG. 1) for measuring water activity of foods, and the disc made of permeable material, with reactive substance added; they have been installed into the container, which has been closed with its respective cover.

FIG. 10 shows a front elevation view of a container with its cover, for discs of permeable material.

FIG. 11 shows a top plan view of the main container body (shown in FIG. 10) for discs of permeable material.

DETAILED DESCRIPTION

Figure 2:
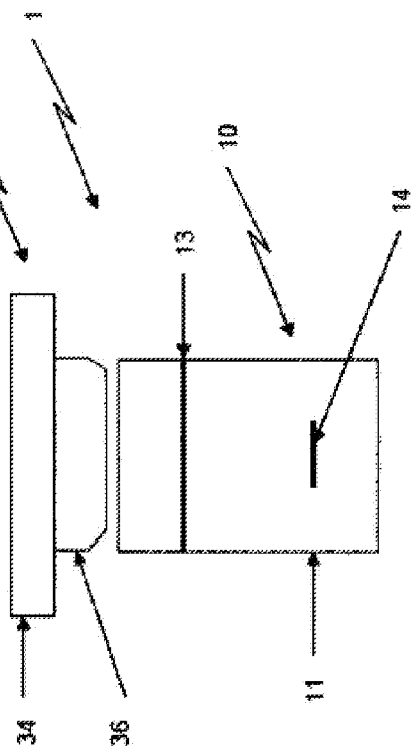
FIG. 2 is a front elevation view of the device (shown in FIG. 1) for measuring water activity of foods, when it is open and having a closure system of the threaded type.

The device for measuring water activity of foods (1) according to the invention comprises one container (10) into which the food sample (23) to be tested is placed, and one disc made of permeable material (20) used as carrier medium for a reactive substance (21) which sense the level of water activity of the sample (23); this substance (21) is placed on the central area of the disc made of permeable material (20). The permeable disc may have a different geometry that a disc, for example it can be used a rectangular strip or square of permeable material. Likewise, the device (1) comprises a threaded cap (30) which is installed in the free end of container (10). Function of this cap is to allow evaporation of water contained in the tested food sample 23, within an apparent isolation from the outside; so that when this water passes through the permeable-material disc (20), and more particularly, when the water comes into contact with the reactive substance (21), the water activity of tested sample (23) stays recorded by means of a color scale.

Container (10) of the device for measuring water activity of foods (1) is formed from a cylindrical-shape container of constant section (11), closed in its bottom end and open in its top end; this container (10) comprises in its external part, near the top end, one threaded section (12) by means of which the cap (30) is installed and secured to the container (10). The container (10) has also, in its bottom part, near the open top end, an annular groove (13), integral to the container (10), on which the permeable-material disc (20) is placed after the food sample (23) to be tested has been placed on the bottom of container (10); this annular groove (13) allows the secure support of permeable-material disc (20) during the test to determine the water activity of the food to be tested. Finally, the container (10) comprises, in its external part and near its bottom end, one marking (14) that can be a protrusion of the same material as that of the container (10), or a marking properly identified made of any visible medium; this marking (14) is used to indicate the level that shall be covered by an homogeneous mixture that forms the food sample to be tested (23), from which the level of water activity is desired.

After having done different tests to define the best location of elements comprised in the container (10) of the device for measuring water activity of foods according to this Invention (1), and more particularly after having amply considered the minimum necessary space for evaporation of water contained in the sample of food to be studied (23), and after taking care that vapors can reach the permeable material (20), impregnating the area where the reactive substance (21) is contained, to allow the full identification of water activity of sample to be tested, following dimensions have been defined as necessary for the container (10), annular groove (13), and marking (14). The cylindrical-shape container, of constant section (11) forming the main body of container (10) shall have 20 mm in its bottom diameter, whereas marking (14) that indicates the level to be covered with the homogeneous mixture of the tested sample (23) shall be at 5-mm over the bottom closed end of container (10), while the annular groove (13) shall be at a height of 25.4 mm measured also from the closed end of container (10). Regarding dimensions of space formed between the upper part of permeable-material disc (20), and the bottom end of cover (30), which stays inside container (10) when the device (1) is closed, these shall be 10-mm maximum height to allow having an adequate space to allow impregnation of the permeable-material disc (20) from its lower part, with vapors coming from the sample to be studied (23).

Regarding dimensions of annular groove (13), it must be indicated that it suffices they allow the supporting of permeable-material disc (20) around its periphery, at the same time allowing a free space at the center of said disc (20), where the reactive substance (21) is concentrated, to allow the easy capture of water vapor given off from the sample under study (23).

It must also be indicated that the necessary length of threaded section (12) is not precisely defined, and can be determined depending on the type of thread used to achieve the closure of container (10) with the cover (30).

In total agreement with the design of container (10) of the device for measuring water activity of foods according to this invention (1), the threaded cover (30) has been shaped; this comprises a first cylindrical section (31) also called gripping part, and a second cylindrical section (32) also called capping part. This second section (32) is called capping because in its inside a thread is set, illustrated with a dotted line in FIGS. 2, 7, and 9; this thread matches the threaded section (12) on external part of container (10), near its upper end; this way, once placed the sample of food under study (23) inside the container (10), up to the marking (14), and the permeable-material disc (20) impregnated with active substance (21) has been placed on the annular groove (13), the threaded cover (30) is installed on the container (10), and the device for measuring the water activity of foods according to the invention (1) is then wholly assembled.

Figure 3:
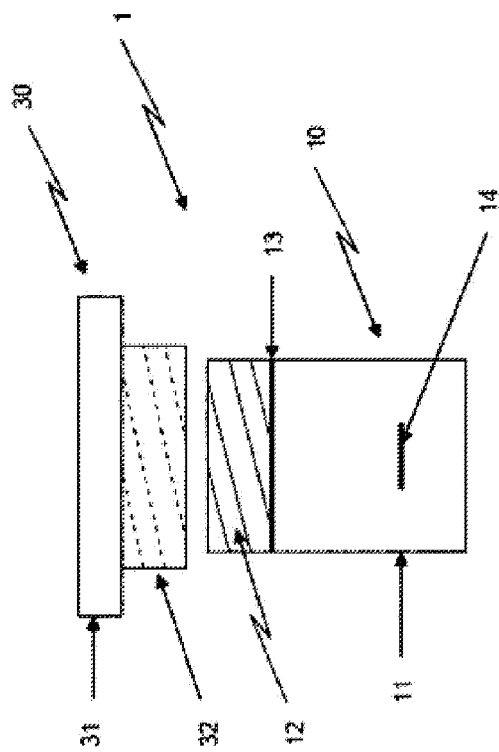
FIG. 3 shows a front elevation view of the device (shown in FIG. 1) for measuring the water activity of foods, when it is open and has an embodiment for the closure.
Figure 1:
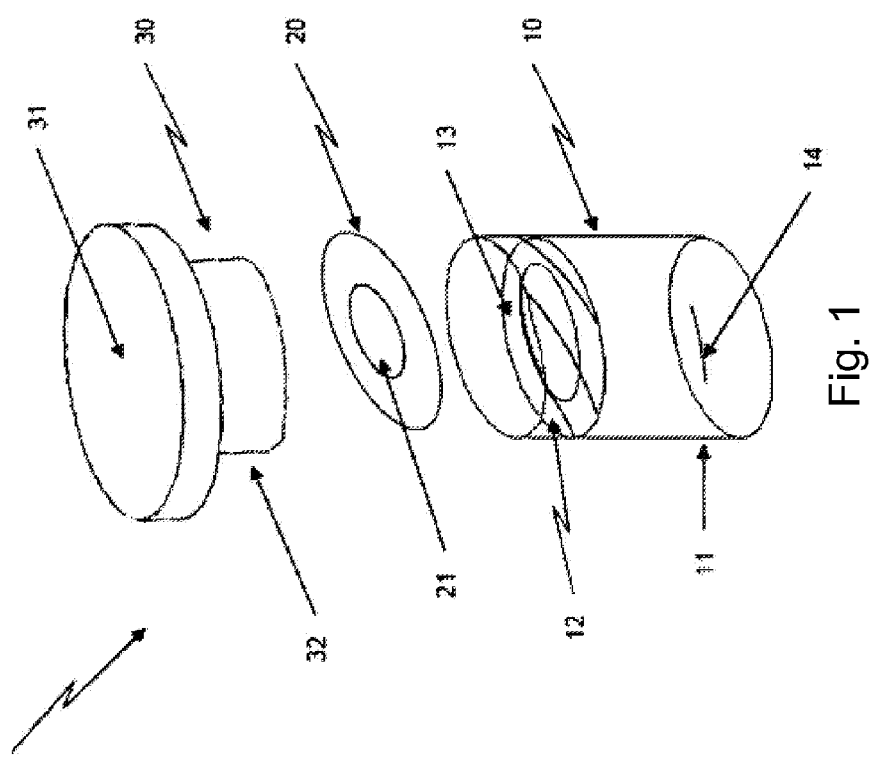
FIG. 1 is an exploded view of elements forming the device for measuring water activity of foods, according to the present invention.

In a preferred embodiment of present invention, as illustrated in FIG. 3, a quick closing cover (33) has been configured which, like in the case of threaded cover (30), it comprises a first cylindrical section (34), also called gripping part, and a second cylindrical section (36), also called capping part.

In this preferred embodiment for the closing system of the device for measuring the water activity of foods according to present invention (1), the capping part (36) is built from a soft material that allows a perfect coupling of the quick closing cover (33) to the inside of container (10), thus achieving the hookup between cover (33) and the container (10) using a slight pressure exerted by the capping part (36) on inner walls of said container (10), and allowing then the necessary isolation between the test space and outside environment.

For this preferred embodiment of the invention, it is important to remark that the container (10) may or may not have the threaded section (12) built on external part, near the top end, in order to secure the closure when using a threaded cover (30), because in this embodiment of the invention the closure of the device for measuring the water activity of foods (1) with a quick-closing cover (33) is made on inner walls of container (10), while in the threaded cover (30) the closure is achieved on external walls of the container (10).

The permeable-material disc (20) used as a carrier medium for reactive substance (21), as mentioned above, is placed on the annular groove (13) inside the container (10), and is made of rice paper or filter paper; these materials have been defined as the most adequate to carry the reactive substance (21) placed on its central part, by placing one or two drops of said reactive substance (21), in such a way that once placed the permeable-material disc (20) on the annular groove (13), central part of the disc (20), where the reactive substance (21) has been placed, is exposed and ready to enter in contact with water vapor coming from the food sample studied (23) and, by a chemical reaction generated during the contact of the evolved water vapor and the reactive substance (21) contained in the permeable-material disc (20), more particularly, in the area impregnated with the reactive substance (21), where a comparison between the color obtained in the disc (20) can be compared with a previously established pattern of colors, the value of water activity of food under study (23) can be obtained.

Taking into account the dimensions of container (10), foreseen so that the permeable-material disc (20) can be easily introduced inside the container (20) and, being at the same time completely supported by the annular groove (13), said disc shall have a diameter of 19 mm.

On the other hand, regarding the reactive substance (21) added in a quantity of one to two drops on central part of permeable-material disc (20), this substance (21) is prepared by dissolving 2 g of zinc chloride (ZnCl2) that has an hygroscopic character, into 1 mL of ethylene glycol, as a solvent vehicle. Also, 0.2 mL of each of following dyes is added: m-cresol purple, bromothymol blue an thymol blue, as acid-base indicators. By using this composition, when hygroscopic salt comes into contact with water vapor coming from the sample under study (23), a dissociation reaction is produced, that can be represented as follows:

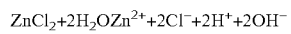

$$ZnCl_2 + 2H_2O \rightarrow Zn^{2+} + 2Cl^- + 2H^+ + 2OH^-$$

One zinc ion is produced, along with two chloride ions, two hydrogen ions and two hydroxyl ions. This dissolution has been represented to help understanding that, when two hydrogen ions come into contact with the dye, a change in color is caused as a consequence of a change of pH in the permeable-material disc (20), and more particularly, in the area where the reactive substance (21) is found; this can be represented as follows:

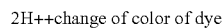

$$2H^+ + \text{change of color of dye}$$

It is important to emphasize that once the permeable-material disc (20) has been impregnated with one or two drops of reactive substance (21), an adequate handling of said disc (20) shall be provided, because if no adequate packaging is procured, the mere contact with ambient humidity will cause a reaction with the hygroscopic salt, and when the permeable-material disc (20) is carelessly placed inside the container (10) for measuring the water activity of a sample of food under study (23), the result obtained will not be the optimum expected one, because of the careless handling caused when letting the ambient humidity react with the hygroscopic salt.

Based on the above, and considering that one objective of the present invention is to provide a device for measuring the water activity of foods, in an easy and rapid manner by using a method that can be applied by any person interested in knowing the water activity of foods, even without having advanced knowledge in the field of food chemistry, and that another objective of this invention is that the device can be readily transported to any place where the sample to be studied is located, it is proposed that a plurality of permeable-material discs (20), impregnated with a reactive substance (21) is placed into a cylindrical container (40) with a cap (45), such as that illustrated in FIGS. 10 and 11, where dimensions of this cylindrical container (40) are such that they allow the storage of 100 permeable-material discs (20) in its inside, in such a manner that, when placing the respective cap (45) on the container (40), the discs (20) are protected from unforeseen reactions with environmental humidity, and at the same time they are ready to be transported to any place where the measurement of water activity of a food sample under study (23) is to be made.

The present invention also comprises one method for measuring the water activity of foods using the here described device. This measuring method for water activity of foods such as meat, dairy, powder and macerated foods, among other, consists of six easily performed steps, that can be done even by persons who have no knowledge in the field of food chemistry, and that in addition the method can be applied at any site where food sample to be studied is found, to obtain dependable and readily interpretable results in reduced waiting times.

Steps comprised in the method for measuring water activity of foods using the above described device of this invention, are the following:

a) In this step, the cover (30) is detached from container (10), and the container (10) is placed on a flat and firm surface.

b) A homogeneous mixture of food under study (23) shall be placed inside the container (10), up to the level indicated by marking (14) of container (10).

c) A permeable-material disc (20), already impregnated with reactive substance (21) shall be moved from container (40) that securely keeps the efficient reactive capability of said disc (20) and the disc shall be placed inside the container (10), resting it on the annular groove (13).

d) Close the container (10) with the threaded cover (30).

e) Wait for a time between 30 and 45 minutes; this is the necessary time taken by reactive substance (21) contained in the permeable-material disc (20) to react with water vapor from the food sample under study (23), thus achieving a permanent color change of permeable-material disc (20), and more particularly of the area where the reactive substance (21) is found.

f) Once the time indicated in the above step is due, detach the threaded cover (31) from the container (10), to allow the extraction of the permeable-material disc (20) with the purpose of comparing the color of said disc (20) with a previously defined color scale, so as to establish the level of water activity of the sample under study (23) according to similarity of colors.

Whereas the permeable-material disc (20) is applied only once, the container (10) and the cover (35) can conventionally be washed and dried to be ready for another measurement of a different food sample.

For the purposes of this invention, in order to define the color- or chromatic scale from which the water activity of sample under study (23) is determined by comparison with the permeable-material disc (20) once the permanent color caused by the sample under study (23) has been achieved according to the method of the invention, one must proceed according to following method:

1. Selection of the Hygroscopic Agent.

Measure the time taken by salts for their hydration when exposed to humidity existing in the environment. Record the increase of weight, in grams, and record the temperature and relative humidity during this stage. In this case, zinc chloride (ZnCl2) was selected.

2. Solvent for the Agent.

Test several solvents, alone and combined, and select the one that, when dissolving in it the salt and exposed to the environment, absorb humidity in the same manner as when not dissolved, and the change of state and change of pH can take place, thus producing a color change. In this case, the selected solvent was ethylene glycol.

Once selected the salt and the solvent, the humidity-absorption kinetics is determined for both components together, measuring the increase in mass, temperature and relative humidity.

3. Selection of Acid-Base Dyes.

To the sample of ZnCl2-ethylene glycol, three dyes are incorporated. The different formulations are impregnated on paper, and placed into micro-environments with different known relative humidity. The pH is recorded by measuring the time taken to reach the equilibrium. In this case, the dyes m-cresol purple, bromothymol blue and thymol blue were selected.

4. Setting Out the Formulation.

Thereafter, the formulation indicated in Table 1 is established.

TABLE 1

| | Component | Quantity |
|---|---|---|
| Solvent | Ethylene glycol | 1 mL |
| Salt | Zinc chloride | 2 g |
| Acid-base indicator | Thymol blue, bromothymol blue, and m-cresol purple | 0.2 g |

5. Testing the Formulation

To evaluate the performance of selected formulation, following sub-steps are done:

a) Weigh and mix the quantities of each reactant.

b) Heat until complete dissolution of zinc chloride, continually mixing to homogenize the indicator. There shall be three solutions, each with a different indicator.

c) Impregnate the paper with the still hot solution, using one capillary tube and placing the different indicators, spaced 5 mm between each formulation.

d) Place the permeable disc within the micro-environment with known relative humidity.

e) Wait until the equilibrium is established (approximately one hour and a half) and record the final color of the paper.

6. Setting of Chromatic Scale.

In specially designed chambers, papers previously impregnated with formulation were placed. To achieve a definition of colors forming the chromatic scale, photographs are taken to micro-environments with different water activities. A designed chamber was made from acrylic resin, to be able to see the final color change. Their dimensions are 45 mm high by 55 mm wide. Two levels were prepared, so as to not allow the direct contact between paper and food sample.

Using the above method the setting of a chromatic scale is possible, to allow the determination of water activity value according to the invention.

To illustrate the present invention, following examples are described, not for the purpose of limiting its applications.

Example 1

Calibration and Obtaining the Chromatic Scale

Several salts with a previously defined water activity (see Table 2) were used to define the chromatic scale used for color determination in the device according to the invention. A significant quantity of sample of each salt in table 2 was placed into the device, and a color scale was obtained, colors varied from rufous brown to light orange. For low water activities (0.225, 0.325), red color was darker; for intermediate water activities (0.571, 0.69), the yellow color was obtained, while for higher water activities (0.84, 0.97), the final color was light orange.

Example 2

Measurement of Water Activity with the Device According to the Invention

For the purpose of verifying the degree of dependability of measurements obtained with the device and method according to the present invention, six measurements of water activity were done on following foods: cereal flakes, yam, biscuits, canned tuna, bananas, apples, watermelon, and lettuce. Measurements were done first with an electronic hygrometer, and then with the device and method proposed in the present invention. The test is conducted under an environmental temperature of between 20-27° C., preferably 25° C. The results obtained are shown in Table 3.

TABLE 2

| Salt | Water activity (25° C.) |
|---|---|
| Lithium bromide | 0.054 ± 0.005 |
| Sodium chloride | 0.113 ± 0.003 |
| Potassium acetate | 0.225 ± 0.003 |
| Manganese chloride | 0.328 ± 0.002 |
| Potassium carbonate | 0.432 ± 0.004 |
| Magnesium nitrate | 0.529 ± 0.002 |
| Cobalt chloride | 0.649 ± 0.036 |
| Sodium nitrate | 0.743 ± 0.003 |
| Potassium bromide | 0.809 ± 0.002 |
| Potassium nitrate | 0.936 0.006 |

TABLE 3

| Food | Electronic hygrometer | Device and method according to the invention |
|---|---|---|
| Cereal flakes | 0.2 | 0.2 |
| Yam | 0.3 | 0.3 |
| Biscuits | 0.38 | 0.4 |
| Canned tuna | 0.61 | 0.6 |
| Bananas | 0.75 | 0.7 |
| Apples | 0.84 | 0.8 |
| Watermelon | 0.93 | 0.9 |
| Lettuce | 0.96 | 0.9 |

From the above results, it can be seen that even with measurement precision of the device and method according to this invention is limited to tenths of a point, while readings obtained with electronic hygrometer are accurate to the hundredths of a point, measurements obtained with the proposed device, using the method here recommended, are very similar to those obtained with the electronic hygrometer; the difference being that the device and method according to present invention are easily accessible and no special care are required, they do not depend from an electric power source, and the device can be transported without great care, as compared with the electronic hygrometer. Also, no involved maintenance is required, and just a cleansing with water and soap can be used with the respective drying.

REFERENCES

1. Campbell, Gaylon S., et. al. 1998. Water activity and dew point temperature measuring apparatus and method. U.S. Pat. No. 5,816,704.
2. Pott, Otto Friedrich. 1977. Measuring device for the water activity of free water containing victuals. U.S. Pat. No. 4,015,463.
3. Sharpe, Anthony N. 1986. Relative humidity or water activity apparatus. CA 1,209,020.

What is claimed is:

1. A device for measuring the water activity of foods, of the type of devices that record water activity with a chemical reaction between water vapor from a food sample, comprising:
   a cylindrical-shape container, of constant cross section, wherein the container is closed in its bottom end and open in its upper end, and includes a closing to close the upper open end,
   the container including an inner integral annular groove on which a permeable-material disc is placed, and
   a marking on an external lower surface of the container that serves to indicate the level up to which should be filled with a homogeneous mixture of food sample under study, for which the water activity level measure is desired, and
   the permeable-material disc carrying:
      a reactive substance formed by dissolving a hygroscopic salt into ethylene glycol as a solvent vehicle, and
      acid-base indicators, consisting of m-cresol purple, bromothymol blue, and thymol blue,
   by means of which a specific color is defined on the permeable-material disc due to a chemical reaction that occurs between water vapor emanated from the sample under study and the chemical components of said reactive substance.

2. The device of claim 1, wherein the closing of the container is selected from a threaded cover and a quick-closing pressure cover.

3. The device of claim 1, wherein the marking is affixed to the container and located at a height of 5 mm from the closed bottom end of the container.

4. The device of claim 1, wherein the marking is configured as a protrusion made of the same material as the container, or identifiable using any visible means.

5. The device of claim 1, wherein the annular groove is placed at a height of 25.4 mm from the closed bottom end of the container.

6. The device of claim 2 wherein the space formed between the upper part of permeable-material disc, and the lower end of the threaded cover, which stays inside the container at the moment of closing the device, has a maximum height of 10 mm.

7. The device of claim 1, wherein the permeable-material disc is made of rice paper or filter paper.

8. The device of claim 1, wherein the permeable-material disc has a diameter of 19 mm.

9. The device of claim 1, wherein
   the reactive substance is added in an amount of one to two drops to a central part of the permeable-material disc, is formed by dissolving 2 g of zinc chloride ($ZnCl_2$) as hygroscopic salt, into 1 mL of ethylene glycol as solvent vehicle, and 0.2 mL of acid-base indicators is added.

* * * * *